United States Patent
Murdeshwar (10) Patent No.: US 10,912,612 B2
(45) Date of Patent: Feb. 9, 2021

(54) SYSTEM AND DEVICE FOR TREATING BODY TISSUE

(71) Applicant: GYRUS ACMI, INC., Southborough, MA (US)

(72) Inventor: Nikhil Murdeshwar, Maple Grove, MN (US)

(73) Assignee: Gyrus Acmi, Inc., Southborough, MA (US)

( * ) Notice: Subject to any disclaimer, the term of this patent is extended or adjusted under 35 U.S.C. 154(b) by 252 days.

(21) Appl. No.: 15/873,084

(22) Filed: Jan. 17, 2018

(65) Prior Publication Data

US 2019/0216544 A1    Jul. 18, 2019

(51) Int. Cl.
*A61B 18/22*     (2006.01)
*A61B 18/20*     (2006.01)
*A61B 17/42*     (2006.01)
*A61B 18/18*     (2006.01)

(52) U.S. Cl.
CPC ...... *A61B 18/22* (2013.01); *A61B 2017/4216* (2013.01); *A61B 2018/1861* (2013.01); *A61B 2018/2005* (2013.01); *A61B 2018/225* (2013.01); *A61B 2018/2255* (2013.01); *A61B 2018/2261* (2013.01)

(58) Field of Classification Search
CPC .............. A61B 18/22; A61B 2018/225; A61B 2018/2261; A61B 2018/1861; A61B 2017/4216; A61B 2018/2005; A61B 2018/2255
See application file for complete search history.

(56) References Cited

U.S. PATENT DOCUMENTS

| | | | |
|---|---|---|---|
| 5,269,777 A | 12/1993 | Doiron et al. | |
| 5,530,780 A | 6/1996 | Ohsawa | |
| 5,707,368 A * | 1/1998 | Cozean | A61B 18/22 606/15 |
| 6,350,276 B1 * | 2/2002 | Knowlton | A45D 44/22 607/101 |
| 2006/0122583 A1 * | 6/2006 | Pesach | A61B 5/0095 606/7 |
| 2006/0184162 A1 * | 8/2006 | Smith | A61B 90/36 606/4 |
| 2006/0242884 A1 | 11/2006 | Talieh | |

(Continued)

FOREIGN PATENT DOCUMENTS

| | | |
|---|---|---|
| CN | 110037794 A | 7/2019 |
| EP | 2249923 A1 | 11/2010 |

(Continued)

OTHER PUBLICATIONS

Extended European Search Report for European Application No. 19150274.9; dated Jun. 14, 2019.

(Continued)

*Primary Examiner* — Gary Jackson
*Assistant Examiner* — Sebastian X Lukjan
(74) *Attorney, Agent, or Firm* — Schwegman Lundberg & Woessner, P.A.

(57) ABSTRACT

A medical device that includes a hand piece; a beam fiber; and a beam disperser located at a distal end of the beam fiber through which beam energy is dispersed. The beam disperser includes one face, or a plurality of substantially planar faces through which the beam energy is dispersed.

19 Claims, 3 Drawing Sheets

(56) References Cited

U.S. PATENT DOCUMENTS

| | | | |
|---|---|---|---|
| 2008/0188835 A1* | 8/2008 | Hennings | A61B 18/22 |
| | | | 604/542 |
| 2009/0204111 A1 | 8/2009 | Bissig et al. | |
| 2011/0160713 A1* | 6/2011 | Neuberger | G02B 6/3801 |
| | | | 606/15 |
| 2011/0301584 A1 | 12/2011 | Beck et al. | |
| 2012/0179229 A1 | 7/2012 | Tettamanti et al. | |
| 2013/0178738 A1* | 7/2013 | Martin | A61B 8/0858 |
| | | | 600/439 |
| 2013/0310819 A1 | 11/2013 | Neuberger et al. | |
| 2016/0058383 A1 | 3/2016 | Hellstrom et al. | |
| 2016/0158573 A1 | 6/2016 | Masotti et al. | |
| 2017/0014267 A1 | 1/2017 | Kern et al. | |
| 2017/0050043 A1 | 2/2017 | Kang et al. | |
| 2017/0326382 A1 | 11/2017 | Seymour et al. | |

FOREIGN PATENT DOCUMENTS

| | | | | |
|---|---|---|---|---|
| EP | 2476460 | A1 | 7/2012 | |
| EP | 3513759 | A1 | 7/2019 | |
| JP | H05161660 | A | 6/1993 | |
| JP | H1052435 | A | 2/1998 | |
| JP | 2019122773 | A | 7/2019 | |
| WO | 02/05722 | A1 | 1/2002 | |
| WO | 2008/134560 | A2 | 11/2008 | |
| WO | 2009/102756 | A1 | 8/2009 | |
| WO | 2008/134560 | A3 | 11/2009 | |
| WO | 2011/060189 | A1 | 5/2011 | |
| WO | WO-2016146237 | A1 * | 9/2016 | A61N 5/0625 |

OTHER PUBLICATIONS

"European Application Serial No. 19150274.9, Response filed Jan. 22, 2020 to Extended European Search Report dated Jun. 14, 2019", 10 pgs.
"Japanese Application Serial No. 2019-005474, Amendment filed Feb. 14, 2019", W/ English Translation, 6 pgs.
"Japanese Application Serial No. 2019-005474, Notice of Reasons for Refusal dated Dec. 17, 2019", W/ English Translation, 6 pgs.
"Japanese Application Serial No. 2019-005474, Notification of Reasons for Refusal dated Jun. 2, 2020", 4 pgs.

* cited by examiner

| Property | Holmium | Thulium | Diode | KTP |
|---|---|---|---|---|
| Depth of penetration | 0.5 mm | 3 mm | 5 mm | 7 mm |
| Wave length | 2100 nm | 2100 nm | 830 nm | 532 nm |
| Cutting | Excellent | Excellent | Good | Poor |
| Coagulation | Ok | Excellent | Good | Excellent |
| Enucleation | Yes | Yes | Possible | Few reports |
| Ablation | Possible | Yes | Yes | Yes |
| Lithotripsy | Excellent | No | No | No |
| Fiber | Flexible | Rigid | Rigid | Rigid |
| Multipurpose | Yes | Yes | No | No |
| Multispecialty | Yes | Yes | Yes | No |
| Tissue for histopathology | Yes | Yes | No | No |
| Portability | No | No | Yes | No |

KTP=Potassium-titanyl-phosphate

SYSTEM AND DEVICE FOR TREATING BODY TISSUE

FIELD

These teachings relate to a system and device for treating body tissue.

BACKGROUND

Menorrhagia is a medical condition defined as abnormally heavy and prolonged menstrual bleeding and pain. For decades, hormone pills or hysterectomy were used to treat menorrhagia.

Recently, surgeons began using various ablation devices to treat menorrhagia by exposing the endometrium to various energy sources (i.e., heat, cold, cryogenics, steam, microwave, and/or RF energy), which typically leads to a decrease in menstrual period bleeding and pain.

However, some currently available ablation device have various shortcomings. For example, some ablation devices require the surgeon to manipulate or move the introducer from side to side and/or rotate the introducer inside the uterus to expose the endometrium to the energy source, which can be cumbersome for the surgeon and painful for the patient. Some ablation devices require a large introducer or shaft diameter to accommodate large current carrying conductors. As can be imagined, a large introducer or shaft diameter can be painful to insert into a patient, and may lead to cervical trauma. Some ablation devices are cumbersome to operate. For example, while some ablation devices are intended for single-handed operation, some devices require plugs to seal the uterus during treatment, which necessitates using a second hand.

In view of the aforementioned, improvement in the art may be desirable.

SUMMARY

These teachings provide a system and device for treating body tissue. The device comprises a beam fiber and a beam disperser. The beam disperser is configured to disperse beam energy from an energy source at an angle relative to a longitudinal axis of the beam fiber to medically effect the walls or tissue of a body cavity. The beam disperser is configured globally disperse the beam energy around or about the longitudinal axis of the beam fiber, or around a circumference of the beam disperser, which may advantageously reduce or eliminate the need for a surgeon to sweep the beam fiber from side to side and/or rotate the beam fiber around or about the longitudinal axis during a medical procedure to medically effect the entire body cavity.

The device comprises a beam disperser. The beam disperser comprises a suitable shape, such as a pyramidal shape, a conical shape, or a polygonal shape. The beam disperser comprises one face, or a plurality of generally planar faces that are each angularly arranged around or about the longitudinal axis. The one face or the plurality of faces may be angled relative to each other to form an obtuse angle or an acute angle. The angular arrangement, which may also be referred to as the cone angle, or the cone angle of the one face or plurality faces, may function to effect or change the width or disperse angle of the beam energy from the beam disperser. Advantageously, a surgeon may select a particular beam disperser based on various factors, such as: the size and/or shape of the body cavity into which the beam disperser is to be inserted, for example.

A medical device is disclosed that includes a hand piece; an introducer extending from the hand piece; and a beam fiber at least partially located inside the introducer. The medical device includes a beam disperser located at a distal end of the beam fiber. The beam disperser includes one or a plurality of substantially planar faces arranged around a longitudinal axis of the beam fiber, through which beam energy is dispensed or dispersed.

A medical device comprising: a hand piece; a beam fiber, and a beam disperser located at a distal end of the beam fiber, through which beam energy is dispersed.

DETAILED DESCRIPTION

These teachings provide a medical system. The medical system may comprise the medical device disclosed herein, the energy source disclosed herein, or both. While these teachings are directed to using the device and system in or during a medical procedure, these teachings may also find use in non-medically related applications that utilize beam energy or IR energy. For examples, these teachings may be used for welding.

These teachings provide a medical device. The medical device may be used to treat or effect an anatomical feature. The anatomical feature may be any anatomical feature, such as a vessel, tissue, vein, artery, a body cavity such as a cervix, a tumor, the like, or a combination thereof. The anatomical feature may be any part of the body that has extra tissue. The medical device may be configured to treat menorrhagia. The medical device may be configured to effect or destroy the endometrium during a procedure treating menorrhagia.

While the device and system disclosed in this application may be used to treat menorrhagia, it is understood that the device and system can be used in other applications as well. For example, the device and system can be used to treat tissue in the bladder, vagina, esophagus, trachea, urethra, ureter, prostate gland, kidney, intestinal growths or abnormal tissues of the intestine, cancerous tissue, etc.

Using the medical device according to these teachings to effect an anatomical feature may mean treating the anatomical feature by ablating, vaporizing, or otherwise removing tissue. Effecting may mean that the tissue or anatomical feature is destroyed, coagulated, and/or denatured.

The medical device may be a global endometrial ablation (GEA) device. The medical device may be an ablation device.

The medical system may comprise one or more energy sources. The medical device may be in electrical communication with one or more energy sources. The energy source may function to produce, supply, and/or transmit energy to the medical device, to the beam fiber, to the beam disperser, or a combination thereof via one or more conductors or wires. The energy source may be part of the medical device, for example, contained within the hand piece. The energy source may be a discrete component that is electrically connected to the medical device with one or more electrical conductors or wires. The energy source may be an AC energy source, a DC energy source, or both. The energy source may be a battery.

Figure 7:
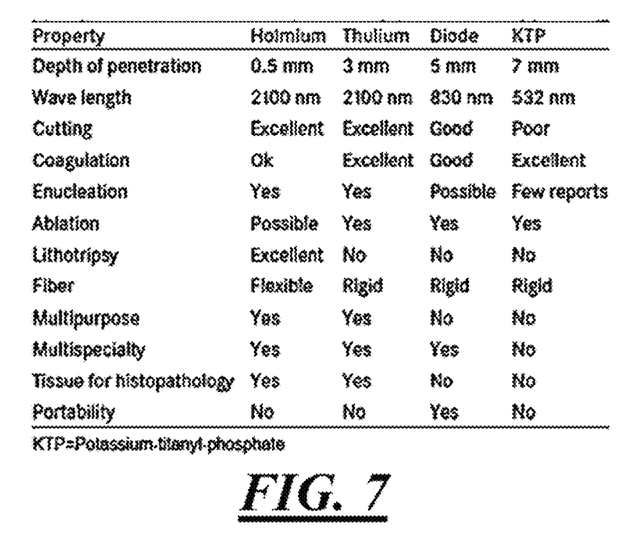
FIG. 7 is a table describing properties of commonly used IR beams in medical devices.
Figure 8:
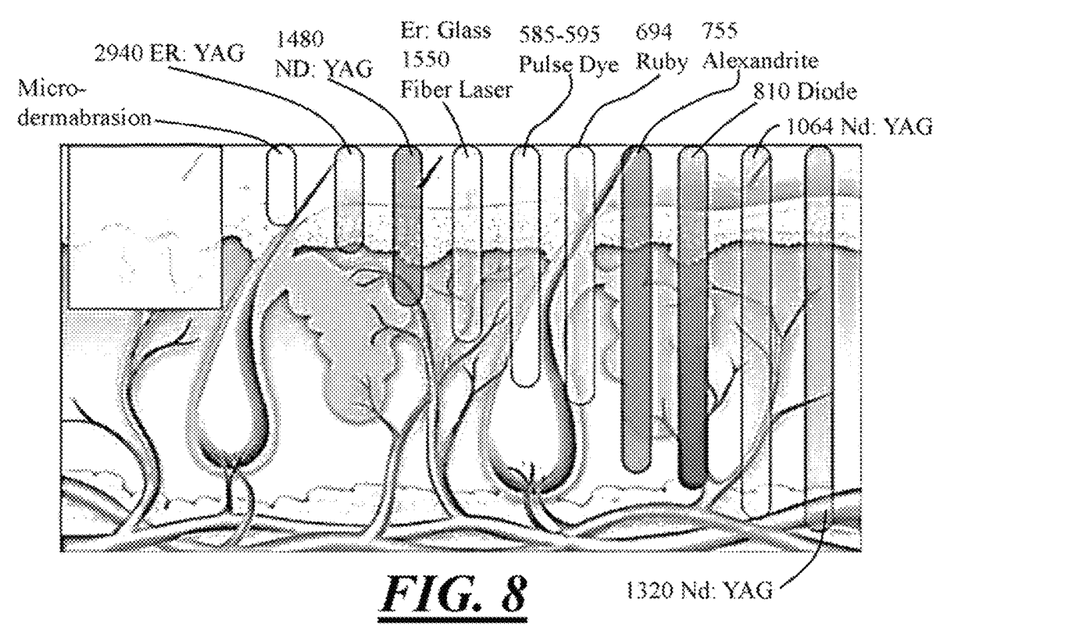
FIG. 8 illustrates a comparison of IR beam tissue penetration as a function of wavelength.

The energy source may be any spectrum of Infrared. For example, the energy source may be a solid-state laser, a diode laser, a gas laser, or a dye laser. The energy source may be based on a potassium-titanyl-phosphate (KTP) crystal, a lithium triborate (LBO) laser, a beta barium borate (BBO), a holmium laser and a thulium laser, or other type of energy source to perform tissue ablation. The energy source may be any of those included in FIGS. 7 and 8.

The energy from the energy source, hereafter "beam energy" may be any suitable energy for effecting an anatomical feature. The beam energy may be infrared or IR energy. The beam energy may be infrared radiation.

Figure 5:
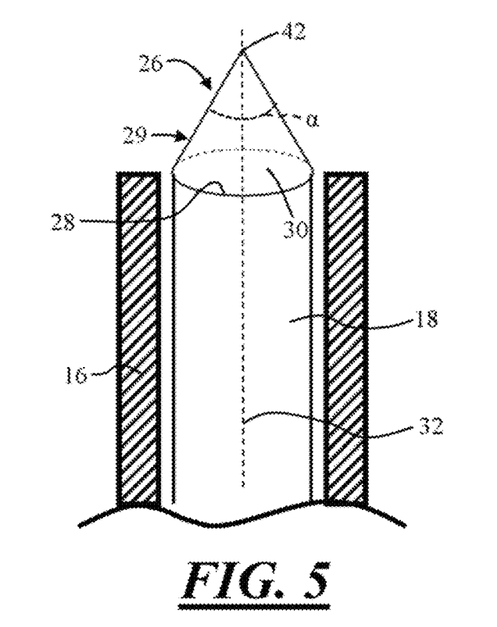
FIG. 5 is a partial perspective view of a beam fiber and beam disperser.

The depth of penetration of the laser or beam energy from the energy source may be on the order of about 0.5 mm (Holmium); about 3.0 mm (Thulium); about 5 mm (Diode); or about 7 mm (KTP). The wavelength of the laser or beam energy may be on the order of about 2100 nm (Holmium or Thulium); about 830 nm (Diode); or about 532 mm (KTP). The penetration depth can vary from about 0.5 mm to about 10 mm. FIG. 5 illustrates penetration depth of the laser or beam energy depending on the spectrum. Depending on the wavelength, the penetration rate or depth will vary.

A laser that is a light source based on stimulated emission of radiation. Radiation from a laser has a high degree of coherence, a narrow bandwidth and is usually, but not necessarily, collimated and polarized. Lasers exist for wavelengths from the x-ray region through to the infrared. Infrared refers to wavelengths between the visible region and the microwave region from approximately 0.7 microns to 1000 microns. Although Infrared lasers exist and are used widely for telecommunications and for cutting metal, the term IR does not in itself imply a laser.

The medical device may comprise a hand piece. The hand piece may function to be held by a user, support or contain one or more components of the medical device. For example, the hand piece may support or contain the beam fiber; the beam disperser, the one or more conductors electrically connecting the beam fiber and/or the beam disperser to the energy source; the energy source; the mechanism for moving the introducer and/or beam fiber, the one or more user controls; the introducer, the balloon; or a combination thereof.

The medical device and/or the hand piece may comprise one or more user controls. Manipulation of the one or more user controls may function to: extend or retract the beam fiber relative to the introducer and/or the hand piece; rotate the beam fiber and/or introducer relative to the hand piece, inflate or deflate the balloon; apply or cease applying or change an intensity of the beam energy; or a combination thereof. The one or more user controls may be one or more switches, levers, buttons, triggers, knobs, rotation wheels, or a combination thereof. The one or more user controls may also be a foot pedal in communication with the medical device, medical system, energy source, or a combination thereof.

The medical device may comprise an introducer. The introducer may function to permit a portion of the device to be inserted into a patient or the anatomy, while a portion of the device remains outside of the patient or anatomy.

The introducer may be a tubular member. The introducer may be an elongated member that extends along a longitudinal axis. The proximal end of the introducer may be connected to the hand piece. The distal end of the introducer may define a mouth or opening through which the balloon, the beam fiber, the beam disperser, or a combination thereof extend. The introducer may have a relatively small diameter. For example, the diameter of the introducer may be on the order of about 10 mm or less, 9 mm or less, 8 mm or less, 7 mm or less, or even 6 mm or less. The diameter of the introducer may be less than 6 mm. Such relatively small sized introducer may function to minimize patient trauma during insertion and/or removal of the introducer into and from the body cavity.

The introducer may be at least partially hollow and may define therein an inner portion. The hollow or inner portion of the introducer is sufficiently sized so that the balloon, one or more beam fibers, one or more beam dispersers, or other instruments, such as a video camera, can reside and/or be moved inside or relative to the introducer.

The introducer may be substantially straight; may include one or more angles, bends or arcs; or a combination thereof. The introducer may be substantially rigid, substantially flexible, substantially resilient, or a combination thereof.

The medical device may comprise one or more beam fibers. The beam fiber may function to receive beam energy from the energy source and then distribute or provide the beam energy to the anatomical feature to medically effect the anatomical feature.

The beam fiber may be an elongated member that extends along a longitudinal axis, which may be the same as, or generally colinear with, the longitudinal axis of the introducer. The beam fiber may be generally centered within the introducer, or the beam fiber may be offset to a side of the introducer to make room for other components of the medical device or system (e.g., balloon, camera, etc.). The beam fiber may be substantially rigid, substantially flexible, substantially resilient, or a combination thereof. One or more beam fibers may be provided inside the introducer.

The one or more beam fibers may be extended or retracted from or into the introducer and/or moved side to side relative to the introducer by manipulating one or more of the user controls. The one or more beam fibers may be rotated about its longitudinal axis, or longitudinal axis of the introducer by manipulating one or more of the user controls.

The beam fiber may be made of a conductor. The beam fiber may be made from typical fiber optic material, such as silicon dioxide, silicon, or fused quartz.

The beam fiber may be at least partially wrapped or surrounded by a sleeve or sheath inside the introducer. The sleeve may be made of a polymeric material, such as plastic or rubber.

The medical device may comprise a mechanism for moving the one or more beam fibers. Moving or moving the beam fiber may mean changing a position of the beam fiber or beam disperser relative to the hand piece, the introducer, and/or the body cavity. Moving or moving the beam fiber may mean moving, changing, and/or displacing the beam fiber or beam disperser along a length of the introducer, about or around the longitudinal axis (i.e., rotationally) of the beam fiber and/or introducer, from side to side within the introducer or body cavity, or a combination thereof. The mechanism may be located inside the hand piece, the introducer, or both.

The mechanism may comprise a motor. The mechanism may comprise a shaft, pin, or reel about which a portion of the beam fiber is wound. Rotation of the shaft, pin, or reel, via a motor, for example, may function to move the beam fiber and/or the beam disperser. The motor may be turned ON or energized by manipulating one or more of the user controls. The mechanism may comprise a pulley about which the beam fiber is wrapped, and the beam fiber is released or allowed to extend into the body cavity as the medical device is inserted into a body cavity. Alternatively, the shaft, pin, or wheel may be manually wound and unwound with a rotation wheel or knob or other user control to move the beam fiber into and out of the introducer, or a sleeve or sheath that may contain the beam fiber.

The medical device may comprise one or more beam dispersers. The beam disperser may function to disperse, distribute, dispense, discharge, diffuse, transmit, emit, spread, or otherwise provide (hereafter "disperse") beam energy, also referred to herein as 'dispersed beam energy', from the beam fiber to the site of interest.

The beam energy may be dispersed from or via the beam disperser along a longitudinal axis of the beam fiber and/or beam disperser, axially from the beam fiber and/or beam disperser; radially from the beam fiber and/or beam disperser; circumferentially from the beam fiber and/or beam disperser, to one or more sides or places of the beam fiber and/or beam disperser; or a combination thereof.

The beam disperser may extend from a distal end of the beam fiber. The beam disperser may be integrally formed with the beam fiber, or mechanically attached thereto via one or more suitable fasteners (gluing, bonding, welding, etc.).

The beam disperser may comprise a conical or pyramidal shape. The beam disperser may have a polygonal shape. The beam disperser may have a triangular shape (three-sided); a quadrilateral shape (four-sided; a pentagonal shape (five-sided); a hexagonal shape (six-sided); a septagonal shape (seven-sided); octagonal shape (eight-sided); a nonagonal shape (nine-sided); decagonal shape (ten-sided); etc.

The beam disperser may comprise a surface having one or a plurality of faces. The one or plurality of faces may surround or may be arranged around or about a longitudinal axis of the beam disperser, beam fiber, introducer, or a combination thereof. When a plurality of faces is presented, each of the faces may be arranged at an angle relative to opposing faces. The angle of the surface or the faces relative to one another may be referred to as cone angle. The cone angle is identified as alpha $\alpha$ in the appended FIGS. 3, 4, 5. The cone angle, or the angle of one face relative to an opposing face may be an acute angle on the order of about 20 degrees or more, 30 degrees or more, 40 degrees or more, 50 degrees or more, 60 degrees or more, 70 degrees or more, 80 degrees or more, or any angle less than 90 degrees. The cone angle, or the angle of the faces relative to each other may be an obtuse angle that is larger than 90 degrees and less than 180 degrees. For example, the cone angle or angle of the faces relative to each other may be on the order of less than about 180 degrees, less than 170 degrees, less than 160 degrees, less than 150 degrees, less than 140 degrees, less than 130 degrees, less than about 120 degrees.

The cone angle, or the angle of one face relative to an opposing face may be the same for all faces of the beam disperser. However, due to tolerances and/or manufacturing variations, some of the faces may have a cone angle or the angle of one face relative to other faces may be slightly different.

The cone angle, or the cone angle of the one face or plurality faces, may function to effect or change the width or disperse angle of the beam energy from the beam disperser. That is, a smaller cone angle may result in a wider beam angle, and a larger cone angle may result in a smaller beam angle. By providing beam dispersers with various cone angles, which function to vary the beam angle, a surgeon may select a particular beam dispenser geometry to have an optimal beam angle output during a medical procedure.

The faces may be generally planar. The faces may be triangular-shaped, where a base of the faces is located at the distal edge of the beam fiber, and the vertex or apex is located at a distal-most end of the beam disperser. The vertex or apex may be generally pointed, or the vertex or apex may be rounded to prevent trauma to the body cavity during insertion of the beam disperser into the body cavity.

Due to the faces being arranged around or about a longitudinal axis of the beam disperser, beam fiber, introducer, or a combination thereof, the beam energy is dispersed globally around or about the longitudinal axis or around a circumference of the beam disperser. This means that the beam energy is dispersed approximately 360 degrees around the longitudinal axis. Advantageously, this means that the beam fiber and/or beam disperser need not be rotated about its longitudinal axis in order to provide beam energy globally or around or about the longitudinal axis. Advantageously, this means that the beam fiber and/or beam disperser need not be manually traversed or moved side to side and/or front to back inside the body cavity in order to provide beam energy globally or around or about the longitudinal axis. This may function to save time during a medical procedure and/or reduce complexity in the medical device.

The beam disperser, the faces, or both may function to disperse, distribute, dispense, transmit, or provide beam energy, also referred to as 'dispersed beam energy', at an angle relative to a longitudinal axis of the beam disperser, beam fiber, introducer, or a combination thereof. The angle of the beam energy, or the dispersed beam energy, or $\beta$ in these FIGS, may be between about 15 degrees and about 75 degrees. The dispersed beam energy, beta $\beta$ may depend on the cone angle alpha $\alpha$.

The medical device may comprise one or more balloons. The balloon may function to distend or deflect tissue or walls defining or surrounding the body cavity. The balloon may function to protect the beam fiber and/or beam disperser from bending or damage, and to lower the risk of anatomical shadows that may reduce the effectiveness of treatment.

The balloon may be attached to a distal end of the introducer, hand piece, or both. The balloon may be contained within the introducer when the balloon is not inflated or in a deflated state. The balloon may be inflated or filled by manipulating one or more of the user controls. The balloon may be inflated by increasing pressure of the inside of the balloon with a fluid or gas. The fluid or gas may be supplied by a fluid or gas source that is in fluid communication with the balloon. In the inflated state, the balloon substantially conforms to the body cavity. For example, in the inflated state, the balloon is adapted to conform to the shape of body cavity of the patient, for example, the vagina, anal cavity, esophagus, trachea, bladder.

The balloon may be formed from a suitable biocompatible and distensible material. For example, the balloon may be formed from silicone, PET, polyurethane, rubber, or the like.

The balloon may be substantially clear or transparent so that the balloon does not interfere with the beam energy that is dispersed from the beam disperser and the balloon is not damaged by the beam energy. The beam fiber, beam disperser, or both is located inside of the balloon when the balloon is inflated, the body cavity is distended, and the beam energy is dispersed from the be a disperser.

Figures 1, 2:
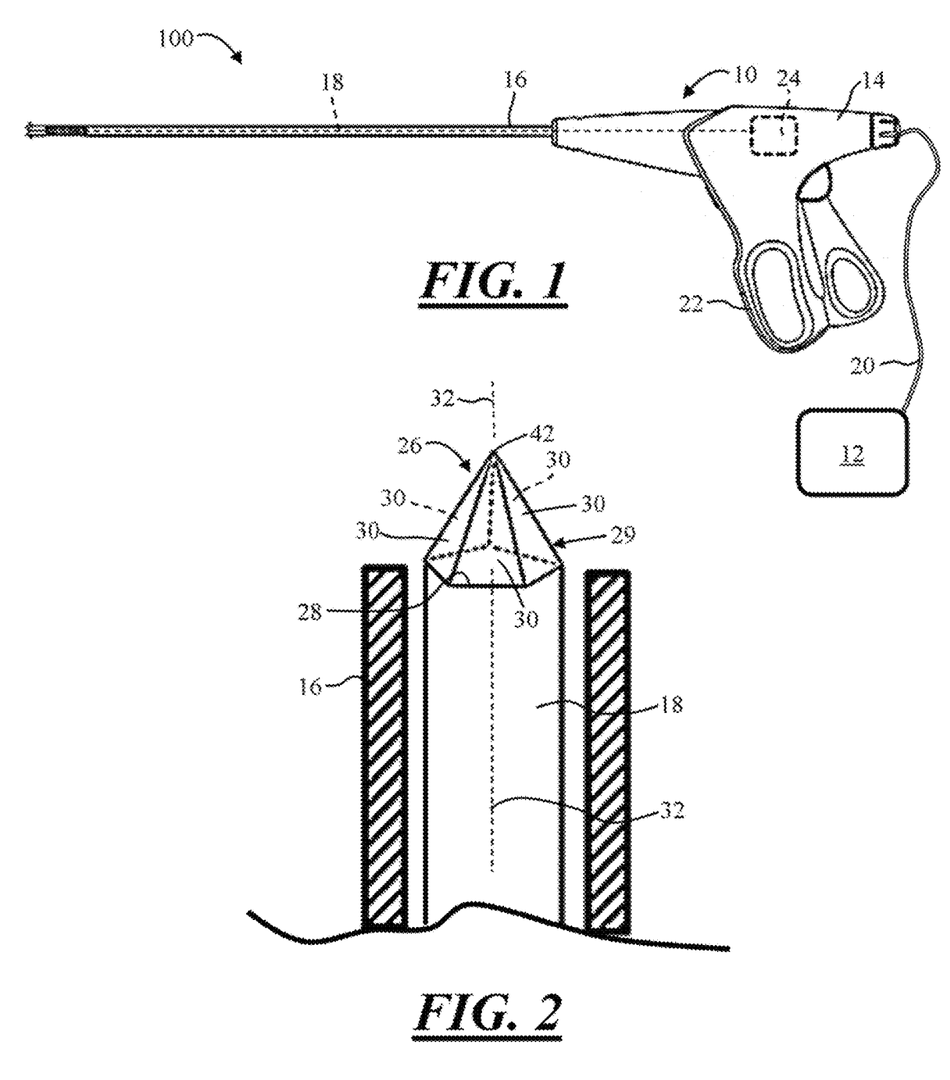
FIG. 1 is a side view of a medical instrument.
FIG. 2 is a partial perspective view of a beam fiber and beam disperser.

FIG. 1 illustrates an exemplary medical system 100. The medical system 100 comprises a medical device 10 and an energy source 12. The medical device 10 comprises a hand piece 14 and an introducer 16 extending from the hand piece 14. A beam fiber 18 is at least partially located within the hand piece 14 and the introducer 16. The beam fiber 18 is electrically connected to the energy source 12 via one or more electrical conductors 20. The hand piece 14 comprises one or more user controls 22 for operating and/or controlling the medical system 100, the medical device 10, and/or the energy source 12. Inside the hand piece 14, the medical device 10 comprises a mechanism 24 for moving the beam fiber 18.

FIG. 2 illustrates a distal portion of the beam fiber 18 and a distal portion of the introducer 16. A beam disperser 26 is connected to and/or extends from a distal end 28 of the beam fiber 18. The beam disperser 26 comprises a conical shape and/or a polygonal shape. The polygonal shape of the beam disperser 26 may be a pentagonal shape.

The beam disperser 26 comprises a surface 29 that extends from the distal end 28 of the beam fiber 18 and terminates at an apex or vertex 42. The surface 29 is arranged around or about a longitudinal axis 32 of the beam fiber 18, the beam disperser 26, and/or the introducer 16. The surface 29 comprises a plurality of substantially planar faces 30 that are arranged around or about a longitudinal axis 32. Each of the planar faces 30 are angled relative to each other and angled relative to the longitudinal axis 32. As will be discussed further below, beam energy from the energy source 12 is configured to be dispersed through the surface 29 and/or the planar faces 30. Because the faces 30 are arranged around or about the longitudinal axis 32, the beam energy is angularly dispersed through the faces 30 around an entire circumference of the beam disperser 26. Preferably little or no beam energy is dispersed through the apex 42, for example, along the longitudinal axis 32 and/or in a 12 o'clock direction relative to the orientation illustrated in FIG. 2. A suitable cap or seal that is configured to block the beam energy may be provided at or over the apex 42 to minimize or prevent the beam energy from being dispended through the apex 42 along the longitudinal axis 32.

Figure 3:
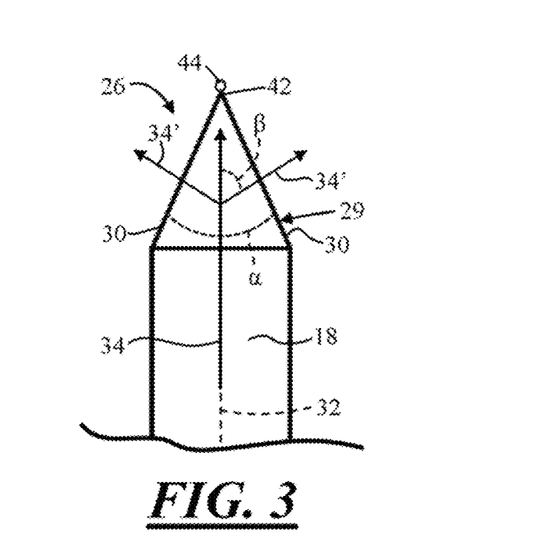
FIG. 3 is a partial side view of a beam fiber and beam disperser.

FIG. 3 illustrates a distal portion of the beam fiber 18 and a distal portion of the beam disperser 26. The surface 29 of the beam disperser 26 is made up of a plurality of planar faces 30, which are arranged at an angle α relative to an opposing face 30. The angle α, which may also be referred to as a cone angle, is an acute angle. Beam energy 34 from the energy source 12 (FIG. 1) is angularly dispersed through the surface 29 and/or the planar faces 30. That is, relative to the longitudinal axis 32, the dispersed beam energy 34' is angularly dispersed from the faces 30 at an angle β. A cap or seal 44 may be provided over the apex 42 to minimize or prevent beam energy from being dispended through the apex 42 along the longitudinal axis 32, for example in the 12 o'clock direction in the orientation illustrated in FIG. 4. A similar cap or seal 44 may be used with any of the other FIGS. disclosed herein.

Figure 4:
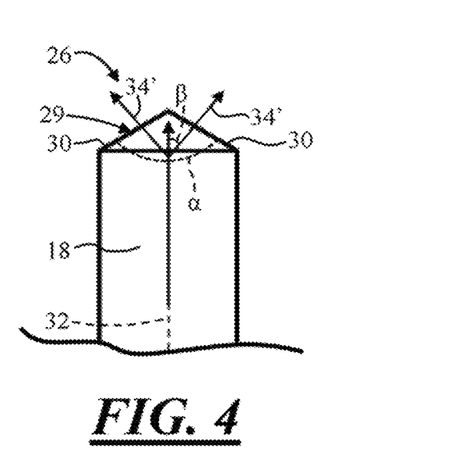
FIG. 4 is a partial side view of a beam fiber and beam disperser.

FIG. 4 illustrates a distal portion of the beam fiber 18 and a distal portion of the beam disperser 26. The surface 29 of the beam disperser 26 is made up of a plurality of planar faces 30, which are arranged at an angle α relative to an opposing face 30. The angle α, which may also be referred to as a cone angle, is an obtuse angle. Beam energy 34 from the energy source 12 (FIG. 1) is angularly dispersed through the surface 29 and/or the planar faces 30. That is, relative to the longitudinal axis 32, the dispersed beam energy 34' is angularly dispersed from the faces 30 at an angle β. Comparing FIG. 3 to FIG. 4, the acute cone angle α of FIG. 3 disperses a wider beam 34' than the obtuse cone angle α of FIG. 4.

FIG. 5 illustrates a distal portion of the beam fiber 18 and a distal portion of the introducer 16. A beam disperser 26 is connected to and/or extends from a distal end 28 of the beam fiber 18. The beam disperser 26 comprises a conical shape. The beam disperser 26 comprises a surface 29 that extends from the distal end 28 of the beam fiber 18 and terminates at an apex or vertex 42. The surface 29 has a single face 30 that is arranged around or about a longitudinal axis 32 of the beam fiber 18, the beam disperser 26, and/or the introducer 16. The angle α, which may also be referred to as a cone angle, is an acute angle. The face 30 is angled relative to the longitudinal axis 32. A tangent of the face 30 at any portion may is angled at an angle α, which may an acute angle as illustrated (similar to FIG. 3), or the angle α may be obtuse angle (similar to FIG. 4). The size or magnitude of the angle α affects the beam dispersed angle β, as was discussed above at FIGS. 3 and 4. As will be discussed further below, beam energy from the energy source 12 is configured to be angularly dispersed through the surface 29 and/or the single face 30 around an entire circumference of the beam disperser 26. Preferably little or no beam energy is dispersed through the apex 42, for example, along the longitudinal axis 32 and/or in a 12 o'clock direction in the orientation illustrated in FIG. 5. A suitable cap or seal, like the one illustrated in FIG. 3, may be provided over the apex 42 to minimize or prevent beam energy from being dispended through the apex 42 along the longitudinal axis 32.

Figure 6:
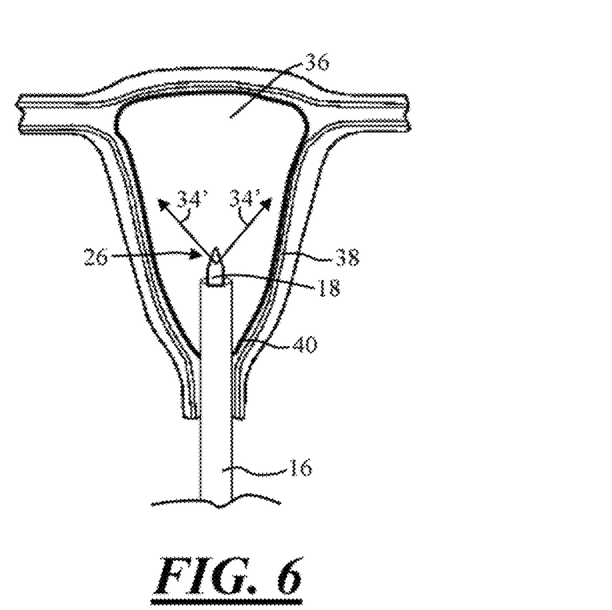
FIG. 6 is a cross-sectional view of a body cavity and a portion of the introducer, beam fiber, and beam disperser located inside the body cavity.

FIG. 6 illustrates a body cavity 36 that is a uterus. During a medical procedure, the introducer 16 is inserted into the body cavity 36. The medical device 10 may comprise an inflatable balloon 38. After the introducer 16 is inside the body cavity 26, the balloon 38 may be inflated to expand the walls 40 of the body cavity 36, as illustrated. Beam energy 34' from the energy source 12 (FIG. 1) is angularly dispersed from the beam disperser 26 (i.e., through the surface 29 or the face(s) 30), through the balloon 38, and onto the walls 40 or tissue lining the body cavity 36, which may be the endometrium of the uterus, to medically effect the walls 40. The beam disperser 26 may be any one or more of the beam dispersers described and/or illustrated herein.

During the medical procedure, one or more of the user controls 22 may be manipulated to move the introducer 16 and/or the beam fiber 18 inside the introducer.

For example, manipulating one or more of the user controls 22 may move the introducer 16 relative to the hand piece 14 in a proximal and distal direction and/or in a lateral direction side to side to medically effect an entire length of the walls 40 of the body cavity 36 with the dispersed beam energy 34'. The beam fiber 18 may or may not be moved with the introducer 16 during this time. Manipulating one or more of the user controls 22 may cause the mechanism 24 (FIG. 1) to move the beam fiber 18 relative to the hand piece 14 in a proximal and distal direction to medically effect the entire walls 40 of the body cavity with the dispersed beam energy 34'. The introducer 16 may or may not be moved with the introducer 16 during this time. Manipulating one or more of the user controls 22 may cause the mechanism 24 or another mechanism to rotate the beam fiber 18 and/or the beam disperser 26 relative to the introducer and/or hand piece 14 about the longitudinal axis 32 to medically effect the entire walls 40 of the body cavity with the dispersed beam energy 34'. Manipulating one or more of the user controls 22 may turn ON or OFF the beam energy from the energy source 12. Manipulating one or more of the user controls 22 may change the strength or intensity of the beam energy supplied by the energy source 12 and/or dispersed from the beam disperser 26. Manipulating one or more of the user controls 22 may inflate and/or deflate the balloon 38.

LISTING OF REFERENCE NUMERALS 10 medical device
12 energy source
14 hand piece
16 introducer
18 beam fiber
20 electrical conductors
22 user controls
24 mechanism
26 beam disperser
28 distal end of beam fiber 18
29 surface
30 face of surface 29
32 longitudinal axis
34 beam energy
34' dispersed beam energy
36 body cavity
38 balloon
40 walls of body cavity 36
42 apex or vertex
44 cap or seal
100 medical system The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

By use of the term "may" herein, it is intended that any described attributes that "may" be included are optional.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. A medical device comprising:
   a hand piece;
   a beam fiber;
   a beam disperser located at a distal end of the beam fiber, through which beam energy is dispersed, wherein the beam disperser comprises a surface arranged around a longitudinal axis of the beam fiber and angled relative to the longitudinal axis, wherein the surface comprises a plurality of substantially planar faces arranged around the longitudinal axis of the beam fiber and defines an apex at a distal-most end of the beam disperser, wherein the beam energy is dispersed from each of the planar faces at an angle relative to the longitudinal axis that is between 15 and 75 degrees;
   an introducer extending from the hand piece, wherein the beam fiber is partially located inside the introducer;
   a first user control that is operable to move the introducer relative to the hand piece; and
   a second user control that is operable to move the beam fiber into and out of the introducer relative to the hand piece.

2. The medical device according to claim 1, wherein the beam energy is IR energy.

3. The medical device according to claim 1, wherein each of the substantially planar faces is arranged at an angle relative to an opposing planar face, the angle is a cone angle.

4. The medical device according to claim 3, wherein the cone angle is an acute angle.

5. The medical device according to claim 3, wherein the cone angle is an obtuse angle.

6. The medical device according to claim 1, wherein the beam disperser comprises a pentagonal shape and the plurality of substantially planar faces comprises five substantially planar faces.

7. The medical device according to claim 1, wherein the surface comprises five substantially planar faces.

8. The medical device of claim 1, further comprising a balloon.

9. A medical system comprising an energy source supplying beam energy to the medical device according to claim 1.

10. The medical device of claim 1, further comprising a cap member disposed at the apex of the beam disperser and configured to minimize or prevent beam energy from being dispensed through the apex along the longitudinal axis.

11. The medical device of claim 1, wherein the first user control is operable to move the introducer in a proximal direction and a distal direction relative to the hand piece.

12. The medical device of claim 11, wherein the first user control is further operable to move the introducer in a lateral direction relative to the hand piece.

13. The medical device of claim 1, wherein the second user control is operable to rotate at least one of the beam fiber or the beam disperser relative to the introducer about the longitudinal axis of the beam fiber.

14. A medical device comprising:
a hand piece;
a beam fiber;
a beam disperser located at a distal end of the beam fiber, through which beam energy is dispersed, wherein the beam disperser comprises a surface arranged around a longitudinal axis of the beam fiber and angled relative to the longitudinal axis, and wherein the surface comprises a plurality of substantially planar faces arranged around the longitudinal axis of the beam fiber and defines an apex at a distal-most end of the beam disperser;
a cap member disposed at the apex of the beam disperser and configured to minimize or prevent beam energy from being dispensed through the apex along the longitudinal axis;
an introducer extending from the hand piece, wherein the beam fiber is partially located inside the introducer;
a first user control that is operable to move the introducer relative to the hand piece; and
a second user control that is operable to move the beam fiber into and out of the introducer relative to the hand piece.

15. The medical device of claim 14, wherein the first user control is operable to move the introducer in a proximal direction and a distal direction relative to the hand piece.

16. The medical device of claim 15, wherein the first user control is further operable to move the introducer in a lateral direction relative to the hand piece.

17. The medical device of claim 14, wherein the second user control is operable to rotate at least one of the beam fiber or the beam disperser relative to the introducer about the longitudinal axis of the beam fiber.

18. The medical device of claim 14, wherein the beam energy is IR energy.

19. The medical device of claim 14, further comprising a balloon.

* * * * *